United States Patent
Yong

(10) Patent No.: US 7,666,667 B2
(45) Date of Patent: Feb. 23, 2010

(54) SAFE SELF-CONTAINED BIO-MOLECULAR SAMPLING AND TRANSPORTATION SYSTEM UTILIZING A DOCKING MECHANISM

(76) Inventor: Peter A. K. Yong, 3426 Onyx St., Torrance, CA (US) 90503

(*) Notice: Subject to any disclaimer, the term of this patent is extended or adjusted under 35 U.S.C. 154(b) by 0 days.

(21) Appl. No.: 11/848,877

(22) Filed: Aug. 31, 2007

(65) Prior Publication Data

US 2008/0058677 A1 Mar. 6, 2008

Related U.S. Application Data

(60) Provisional application No. 60/842,838, filed on Sep. 6, 2006.

(51) Int. Cl.
*C12M 1/26* (2006.01)
*C12M 3/00* (2006.01)
(52) U.S. Cl. .................................................. 435/309.1
(58) Field of Classification Search ............... 435/309.1
See application file for complete search history.

(56) References Cited

U.S. PATENT DOCUMENTS

| 5,163,441 | A | * | 11/1992 | Monthony et al. ........... 600/572 |
|---|---|---|---|---|
| 5,260,031 | A | | 11/1993 | Seymour |
| 5,352,410 | A | * | 10/1994 | Hansen et al. ................. 422/58 |
| 5,609,160 | A | | 3/1997 | Bahl et al. |
| 5,627,071 | A | * | 5/1997 | Triva ......................... 435/307.1 |
| 5,714,341 | A | | 2/1998 | Thieme et al. |
| 5,830,410 | A | * | 11/1998 | Thieme et al. ................. 422/58 |
| 5,874,045 | A | | 2/1999 | Chisum |
| 5,900,379 | A | | 5/1999 | Noda et al. |
| 6,180,395 | B1 | * | 1/2001 | Skiffington et al. ....... 435/287.6 |
| 6,241,689 | B1 | | 6/2001 | Chard et al. |
| 6,840,911 | B2 | | 1/2005 | Sangha |
| 7,114,403 | B2 | * | 10/2006 | Wu et al. .................. 73/864.72 |
| 2002/0001539 | A1 | * | 1/2002 | DiCesare et al. .............. 422/52 |
| 2003/0064526 | A1 | * | 4/2003 | Niedbala et al. ............. 436/165 |
| 2004/0022687 | A1 | * | 2/2004 | Wuske et al. .................. 422/99 |
| 2004/0057876 | A1 | * | 3/2004 | Wuske et al. ................ 422/100 |
| 2005/0059165 | A9 | * | 3/2005 | Davis et al. ................. 436/514 |

FOREIGN PATENT DOCUMENTS

WO WO95/25948 * 9/1995

* cited by examiner

*Primary Examiner*—Walter D Griffin
*Assistant Examiner*—Lydia Edwards
(74) *Attorney, Agent, or Firm*—Walter A. Hackler

(57) ABSTRACT

A safety bio-molecular sampling and transport system utilizing a docking connector mechanism includes a elongate enclosure having open ends along with a collection sponge slidably disposed within the enclosure. A sponge moving piston is provided within the enclosure and is engagable with a plunger handle which is configured for removably engaging the piston and enabling manual sliding of the collection sponge between the position inside of the elongate structure and a position exterior another end of the enclosure. A specimen capsule configured for removably docking to the enclosure is provided for receiving specimen and is sealable for safe and laborless transport thereof.

18 Claims, 5 Drawing Sheets

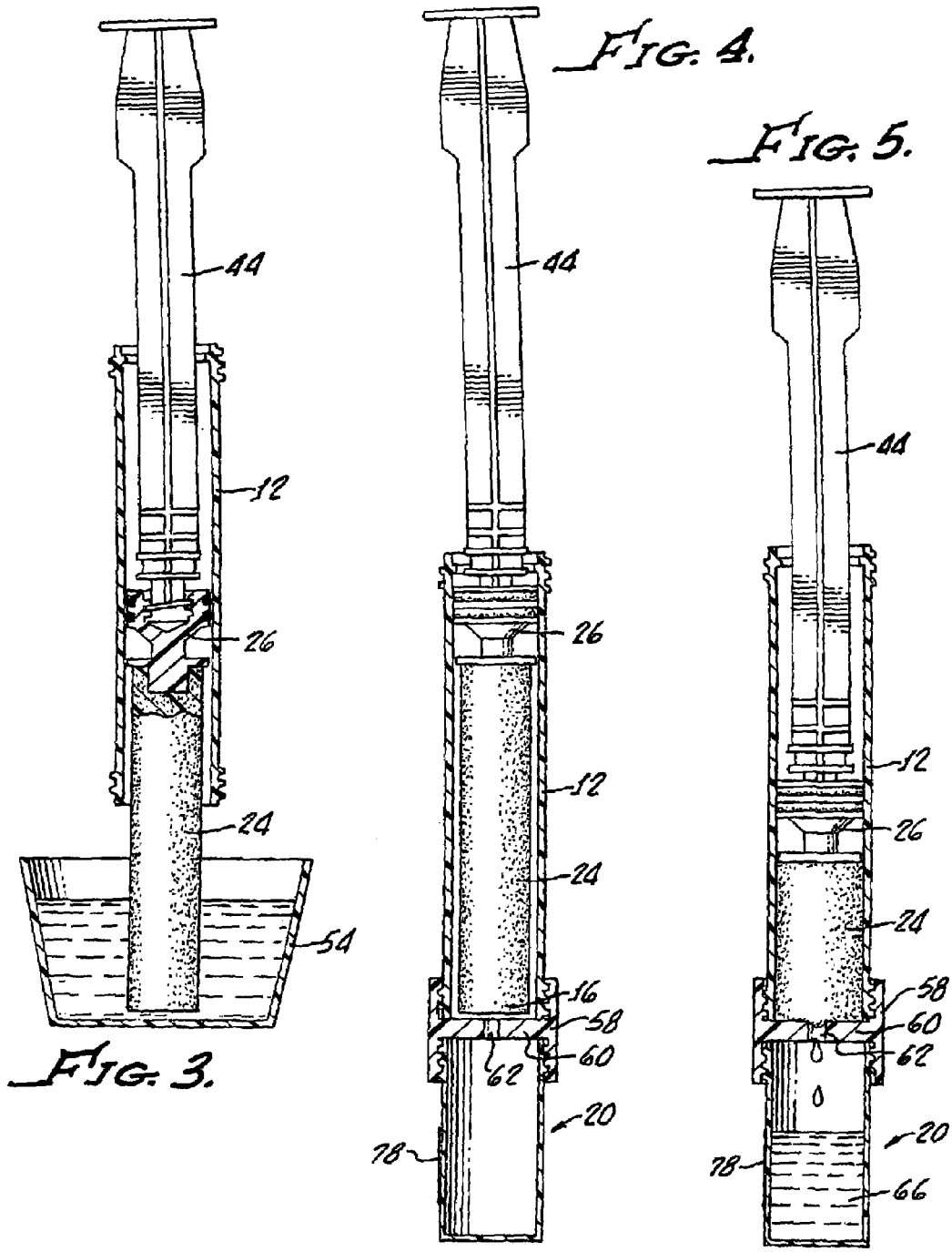

SAFE SELF-CONTAINED BIO-MOLECULAR SAMPLING AND TRANSPORTATION SYSTEM UTILIZING A DOCKING MECHANISM

The present application claims priority from U.S. Ser. No. 60/842,838 filed Sep. 6, 2006. This application is to be incorporated herein in its entirety.

The present invention is generally related to devices for the safe collection of specimens, for example, oral fluids, urine, microbiological specimens, genome DNA, cervical PAP smear samples, or the like, and safe transportation thereof for diagnostic testing including time sensitive testing. More particularly, the present invention provides for a system having an absorbent for the collection of oral fluids or urine and a specimen capsule for enabling closed system transfer of the sample from the absorbent via docking with the capsule with the aid of a docking connector.

Heretofore, bio-molecular sampling and assay for analysis of fluids have typically required at least two different actions. Specifically, the sample, for example urine, saliva, bacteriological, genome DNA, cervical or pap smear sample, is collected and thereafter the collected sample is either stored for later transport into an appropriate reagent for assay in a laboratory in a capsule other than the collection device. Thus, these procedures require multiple steps and components which are often expensive to manufacture and cumbersome for patient use.

With regard to oral fluids and urine, when prior art collection containers are utilized, they are time consuming, multi-action and cumbersome involving transferring of samples. Such additional manipulation necessary for obtaining the required sample often results in contamination either of the sample or medical persons handling the samples.

The bio-molecular sampling and transportation system in accordance with the present invention is closed, i.e. self-contained, compact, leak-proof, tamper resistant, reliable and bar-codeable for insuring integrity of the sample. The system is also simple and easy to use by patients as well as being ergonomically designed and hygienic. In addition, its simplicity leads to an economically produced system.

SUMMARY OF THE INVENTION

A safe and retractable bio-molecular sampling and transportation system in accordance with the present invention utilizes a unique docking mechanism. The system includes an elongate enclosure having open ends with a collection sponge which can be slideably disposed within the elongated closure.

For use in collecting urine, the collection sponge may have a cylindrical shape for direct sampling by soaking from a stream or indirect sampling by soaking from a collection cup. However, for the collection of oral fluids, i.e. saliva, or genome DNA the collection sponge may include a swab with a stem attached thereto. The collection sponge is slidably disposed within the elongate structure and a sponge moving piston is disposed within the elongate structure and has an engageable end disposed proximate one end of the elongate enclosure.

A plunger handle is removably attached to the piston engageable end for enabling manual sliding of the collection sponge between a position inside of the elongate enclosure and a position exterior another end of the elongate enclosure. That is, the sponge is extended from the enclosure for specimen collection and then retracted within the enclosure following collection.

A specimen capsule containing time sensitive diagnostic preservative or reagent, or bacteriological culture medium is provided and removably dockable to another end of the enclosure by using the docking connector thereby enabling leak-proof transfer of the specimen from the sponge into the specimen capsule. In that regard, the specimen capsule may include a perforated baffle with the baffle perforation enabling passage of the specimen therepast into the specimen capsule upon compressing of the collection sponge against the baffle by the piston via the plunger handle. A removable enclosure cap may be provided for sealing the elongate enclosure and a removable specimen capsule cap may be provided for sealing the specimen capsule. In this embodiment, only the specimen capsule is transported to the laboratory.

In one embodiment of the present invention, the plunger handle is stored separate from the elongate enclosure while in another embodiment of the present invention, the plunger handle comprises a tube which is storable within the elongate enclosure between the collection sponge and an inside of the enclosure. This embodiment provides for compact storage.

Preferably, the capsule cap includes a nozzle and the specimen capsule is squeezable, thus enabling dispensing of specimen directly from the capsule through the nozzle. A nozzle cap is also provided.

The system in accordance with the present invention may also include pre-filled active agent or culture medium such as a time sensitive preservative when a time sensitive analysis is to be performed disposed in the specimen capsule for reacting with the specimen when introduce thereinto.

BRIEF DESCRIPTION OF THE DRAWINGS

The advantages and features of the present invention will be better understood by the following description when considered in conjunction with the accompanying drawings, in which:

FIG. 3 is a cross sectional view illustrating the extension of the collection sponge from the enclosure in order to directly or indirectly receive a sample;

FIG. 4 is a cross sectional view illustrating the withdrawal of the collection sponge into the enclosure and the attachment of a specimen capsule attached to the enclosure by a docking connector including a baffle with a perforation therethrough for enabling passage of the specimen into the capsule;

FIG. 5 is a cross sectional view similar to that shown in FIG. 4 illustrating the compression of the collection sponge by the piston via a plunger handle in order to transfer specimen from the sponge through the perforation and into the capsule;

DETAILED DESCRIPTION

Figure 1:
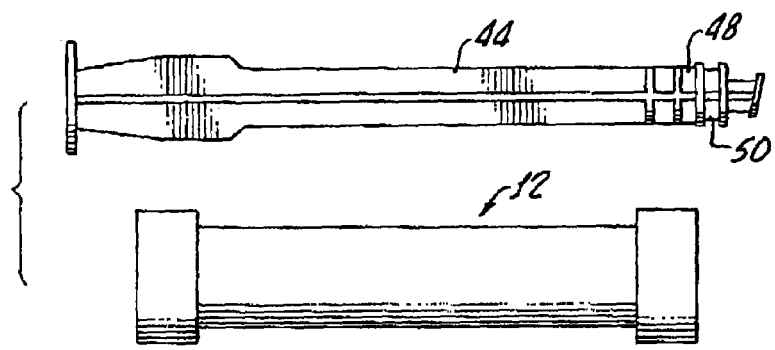
FIG. 1 illustrates elements of a bio-molecular sampling and transportation system in accordance with the present invention generally showing an elongate enclosure with caped ends and a separately stored plunger handle having a piston engagable end.
Figure 2:
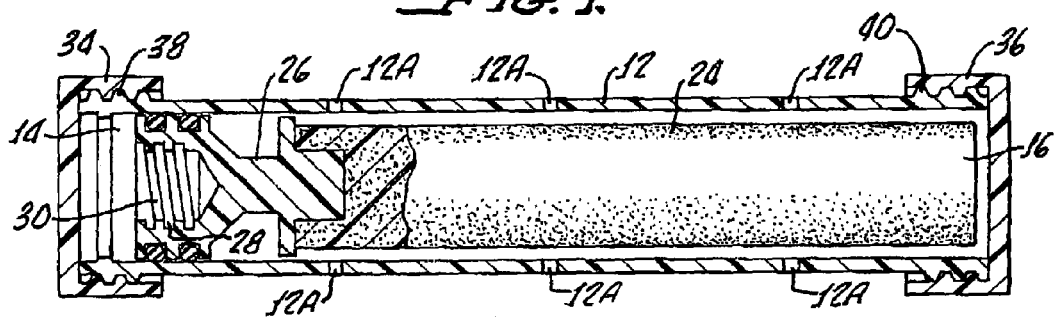
FIG. 2 is a cross sectional view of the elongate enclosure illustrated in FIG. 1 showing a collection sponge slidably disposed within the enclosure along with a sponge moving piston which is disposed within the enclosure and including an engagable end disposed proximate one end of the enclosure and another end attached to the collection sponge.
Figure 6:
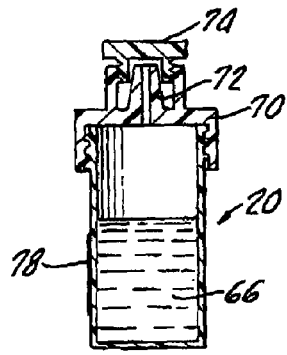
FIG. 6 is a cross sectional view of the capsule along with a capsule cap including a nozzle and a nozzle cap.
Figure 7:
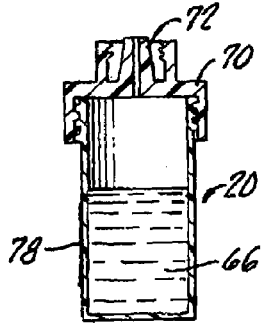
FIG. 7 illustrates the specimen capsule shown in FIG. 6 with the cap removed.
Figure 8:
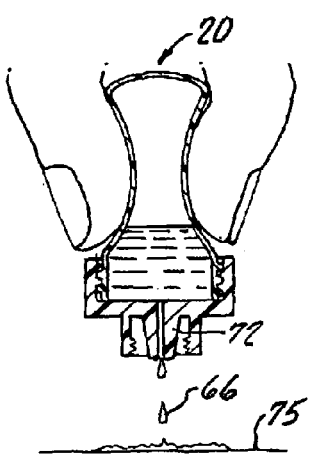
FIG. 8 illustrates the dispensing of specimen from the capsule by squeezing of the specimen capsule.

With reference to FIGS. 1-16, there is shown a safe self-contained bio-molecular sampling and transportation and dispensing system in accordance with the present invention which generally includes an elongate enclosure 12 having open ends 14, 16, as shown in FIGS. 1 and 2, and a specimen capsule 20 shown in FIGS. 6-8.

With reference again to FIG. 2, a collection sponge 24, which may be formed from any suitable absorbent material, is slidably disposed within the elongate enclosure 12 and fixed to a piston 26, also disposed within the enclosure 12, for extending and retracting the sponge 24, as hereinafter described in greater detail. The piston 26 includes an engagable end 28 having threads 30.

Removable enclosure caps 34, 36 threadably 38, 40 engage the enclosure 12 proximate the open ends 14, 16 for sealing the enclosure 12 with the sponge 24 therein before and after use. A separate plunger handle 44, see FIGS. 1, and 3-5 includes a handle end 48 having threads 50 for engaging the piston threads 30 for enabling manual sliding of the collection sponge 24 between a position inside the elongate enclosure 12 as shown in FIGS. 2 and 3 and a position exterior the enclosure end 16 as shown in FIG. 3 for the collection of a specimen. That is, the sponge 24 may be extended and retracted out of and into the enclosure 12.

For illustration purposes only, in FIG. 3 the sponge is shown absorbing a sample from a cup 54, i.e. indirect sample collection. However, it is also well suited for direct collection by receiving a urine stream or insertion into a buccal cavity (not shown) for the collection of oral fluids.

Buccal saliva specimens may be used for DNA testing, HIV testing, drug testing, substance of abuse testing, etc., whereas urine specimens may be utilized for clinical urinalysis, bacterial culture, pregnancy, HIV and other substance of abuse tests. Throat swab specimens in children are important for strep throat infection diagnosis. Endo-cervical swabs are for the diagnosis of women uro-genital pathologies.

With reference to FIGS. 4-8, the specimen capsule 20 is removably dockable to the enclosure proximate the open end 16 by means of a docking connector 58 threadably engaging the enclosure 12 and specimen capsule 20 as shown in FIGS. 4 and 5. The connector 58 may have standard threads for engaging various capsules, even commercially available capsules (not shown). A baffle 60 is provided with at least one perforation, or opening 62, for enabling passage of specimen through the opening 62 and into the capsule 20 upon compressing of the collection sponge 24 against the baffle 60 by the piston 26 via the plunger handle 44 as illustrated in FIG. 5. It should be appreciated that the opening 62 may be of varying size to accommodate various anticipated viscoscities of the specimen preservatives and also the size and shape of the collector tips.

Following the receipt of the urine specimen 66, as shown in FIG. 5, the docking connector 58 is removed and the capsule 20 sealed with a capsule cap 70, (see FIG. 6) which preferably includes a nozzle 72 which may, in turn, be sealed with a cap 74, the capsule 20, the capsule cap being shown in FIG. 7 sans the nozzle cap 74.

Figure 14:
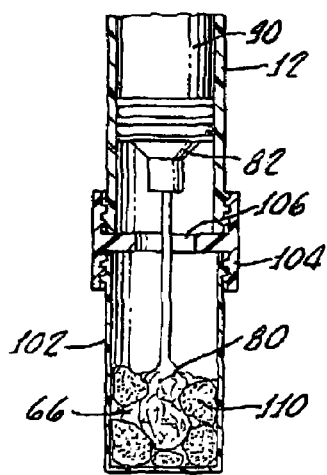
FIG. 14 illustrates the transfer of collected liquid specimen such as saliva into a specimen capsule with the aid of a docking connector which includes a pre-filled active agent for reacting with the specimen.
Figure 14A:
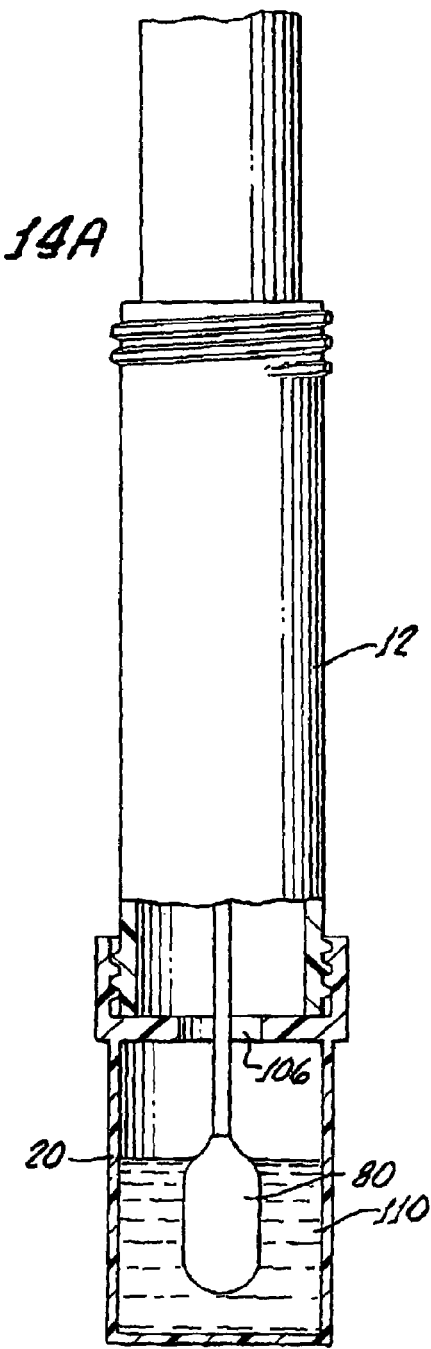
FIG. 14A illustrates the transfer of the capsule and enclosure with the aid of the docking connector together to a laboratory as may be desired when the pre-filled preservative or reagent is in the form of a gel, paste or semisolid colloid reagent used to inter-react with the specimen on the swab.

The specimen capsule 20 may be safely transported with the capsule cap 70 and nozzle cap 74 in place and the enclosure 12 sealed again with the caps 34, 36 for disposal thus enabling sample collection and transport with total security from contamination or spillage. Alternatively, the entire enclosure 12 may be transported to a laboratory with the capsule 20 attached thereto with the docking connector 58, see FIG. 14A. This is important if a gel, colloid, or semi-solid preservative 110 is used. In this case, the swab may be immersed into this preservative 110 until removed for analysis at the lab. If the specimen requires drying, vents 12A in the enclosure 12 may be provided. (See FIG. 2).

Preferably, the capsule is formed from a resilient material enabling squeezing thereof, as shown in FIG. 8, for dispensing of specimen on an assay sheet 76 or a test tube for diagnostic analysis. It should be appreciate that the specimen 66 may be dispensed into any suitable diagnostic device (not shown). A bar code 78 may be provided on the capsule 20 for identification and security tracking purposes.

Figure 9:
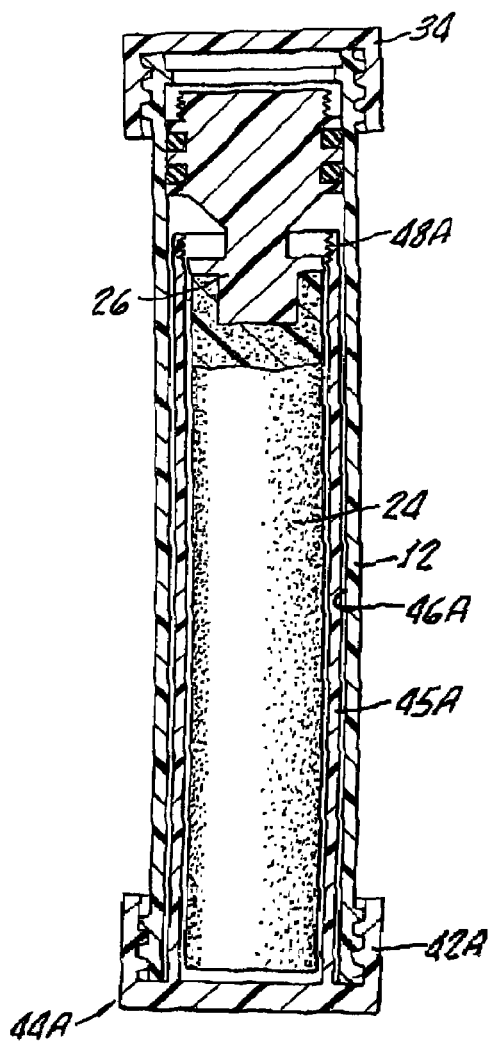
FIG. 9 illustrates another embodiment of the present invention in which the plunger handle includes a tube storable within the elongate enclosure between the collection sponge and an inside of the elongate enclosure.
Figure 10:
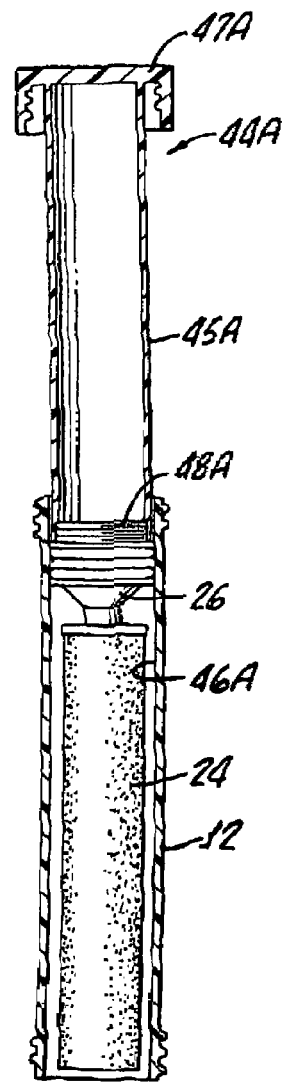
FIG. 10 illustrates the embodiment shown in FIG. 9 with the plunger handle removed from the elongate enclosure and attached to a piston for extending and retracting the collection sponge from and into the elongate enclosure.
Figure 11:
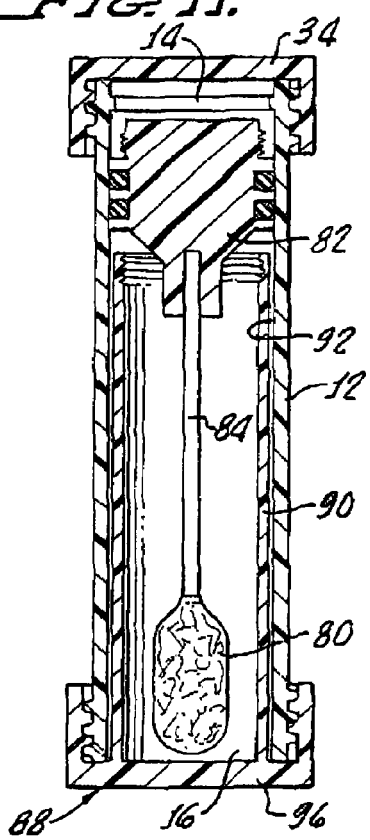
FIG. 11 is a cross sectional view of another embodiment of the present invention in which the collection sponge includes a swab suitable for collection of the saliva from a buccal cavity, genome DNA for crime scene or sexual assault investigation, throat swab for bacterial, viral culture and sensitivity studies, and endocervical specimens such as Clamydia Trichomatis infection and PAP smear examination for cervical cancer.

Another alternative embodiment of the present invention is shown in FIGS. 9 and 10 with common reference characters representing identical or similar components as shown in FIGS. 1 and 2. In this arrangement, a plunger handle 44A includes a tube 45A storable within the elongate enclosure 12 between the sponge 24 and an inside 46A of the elongate enclosure 12. The handle 44A is removably secured to the enclosure 12 by way of a cap 47A. The arrangement provides for compact storage of the enclosure 12 with the tube 45A stored within.

As shown in FIG. 10, when the tube 45A is removed from the enclosure 12 it may be attached by a screw thread 48A to the piston 26 for extending and retracting the sponge 24 from and into the enclosure 12, the sponge 24 being shown inside the enclosure 12 in FIG. 10.

Figure 11A:
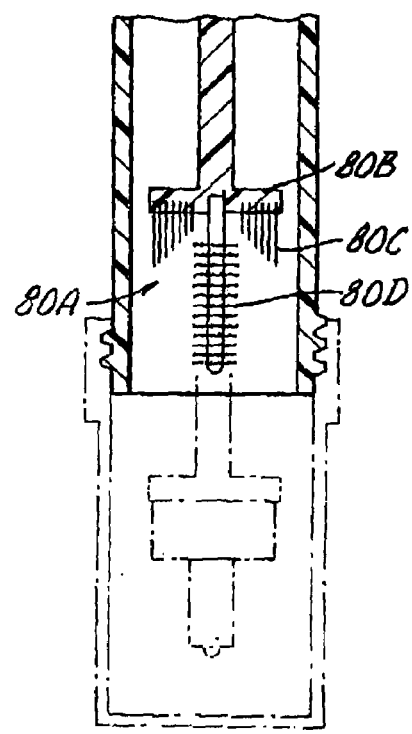
FIG. 11A illustrates a brush specifically designed for PAP smear sampling.

Yet another alternative embodiment of the present invention is shown in FIGS. 11-16. In this embodiment, an absorbent swab 80 is provided which is interconnected with a piston 82 by a stem 84 while initially disposed in the elongate enclosure 12. It should be appreciated that the swab 80 may be of any suitable shape and may include a scraping device, PAP smear brush tip 80A (see FIG. 11A), to facilitate gathering of a specimen from tissue. The PAP smear brush 80A includes a base 80B with peripheral bristles 80C and a central brush 80D to sample both cervical and endo-cervical canal samples simultaneously.

In this embodiment, a plunger handle 88 includes a tube 90 storable within the enclosure 12 between the swab 80 and an inside 92 of the enclosure 12. A handle cap 96 sealably engages the tube at the open end 16 thereof.

As hereinabove noted, this arrangement enables even more compact storage and shipment of the system since the handle 88 does not need separate shipment and storage. On the other hand, in the system shown in FIG. 1, a single handle 44 may be used with any number of enclosures 12.

Figure 12:
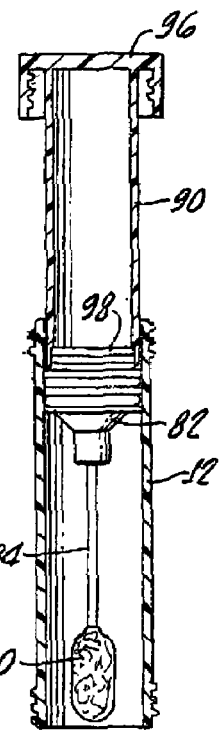
FIG. 12 is a view similar to FIG. 11 with a cap removed from the enclosure enabling extension of the swab from the enclosure.
Figure 13:
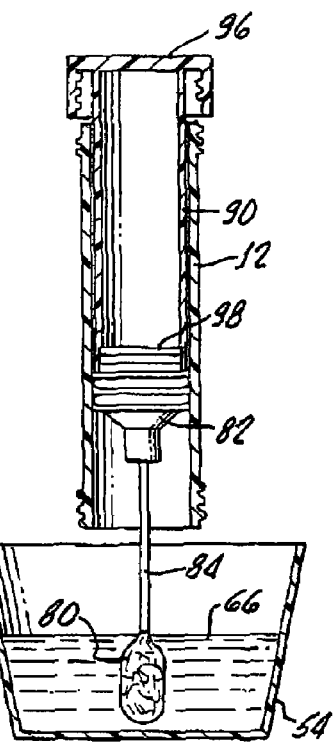
FIG. 13 illustrates an extended swab for collection of saliva, buccal epotheria cells for DNA analysis, or bacterial, viral throat specimen from a patient's mouth (not shown)
Figure 15:
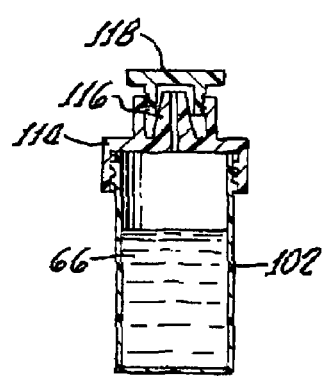
FIG. 15 illustrates the soft compressible capsule along with a capsule cap with nozzle and a nozzle cap.
Figure 16:
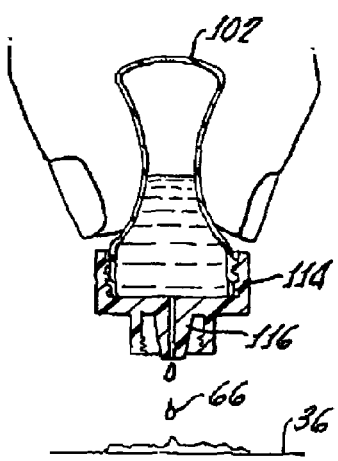
FIG. 16 illustrates dispensing of the specimen treated by the active agent through the nozzle by squeezing of the capsule after agitation to dissolve or react with the active agent.

In operation, as illustrated in FIGS. 12 and 13, the handle 88 is removed from within the enclosure 12 and coupled to the piston 82 by threads 98, or the like. It should also be appreciated that any means of coupling the handle to the 90 to piston 82 may be utilized and be within the scope of the present invention.

As earlier described, the handle tube 90 may be used to manually extend the swab 80 for collection of specimen 66, as illustrated in FIG. 13. Again, the cup 54 shown is merely demonstrative of one way for enabling the swab 80 to absorb the specimen 66 and as indicated earlier, any means for wetting of the swab, i.e. direct or indirect, is to be considered within the scope of the present invention.

Following collection of the specimen 66, the swab 80 is again extended into a specimen capsule 102 through a connector 104 with larger aperture 106. In this embodiment, the capsule 102 may include a liquid, solid, or gel active agent preservative 110 for treating, fixing, or chemically interacting with the specimen 66, as may be desirable for certain diagnostic tests or to preserve the sample during the transportation. The specimen can easily be agitated, by shaking, within the capsule 102 for promoting specimen extraction or eluting mechanism or dissolving the specimen by the agent 110.

Following introduction of the specimen 66 into the capsule 102, the capsule is sealed by a capsule cap 114 having a nozzle 116 with a nozzle cap 118. At this point, the capsule and contents may be further agitated to be either mixed or activate the agent 110 and the specimen 66. Thereafter, sample may be dispensed on the nozzle 116 by squeezing of the capsule 102 as hereinbefore described in connection with FIG. 8.

Although there has been hereinabove described a specific bio-molecular sampling and transporting system and method in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A bio-molecular sampling and transportation system utilizing a docking mechanism, the system comprising:
    an elongate enclosure having open ends;
    a collection sponge slideably disposed within said elongate enclosure;
    a sponge moving piston, disposed within said elongate enclosure, having an engagable end disposed proximate one end of said elongate enclosure;
    a tubular plunger handle storable within said elongate enclosure between said collection sponge and an inside of said enclosure and removably engagable with the piston for enabling manual sliding of said collection sponge between a position inside of said elongate enclosure and a position exterior another end of said elongate enclosure;
    a specimen capsule, removably dockable to the another end of said elongate enclosure, for receiving specimens from said collection sponge, said specimen capsule including a perforated baffle, the baffle perforation enabling passage of specimen therepast into said specimen capsule upon compressing of said collection sponge thereagainst by the piston via said plunger handle;
    removable enclosure caps for sealing said elongate enclosure; and
    a removable specimen capsule cap for sealing said specimen capsule.

2. The system according to claim 1 further comprising a docking connector for removably docking said specimen capsule to said elongate enclosure.

3. The system according to claim 1 wherein the capsule cap includes a nozzle and a nozzle cap.

4. The system according to claim 1 wherein said specimen capsule is squeezable for enabling dispensing of specimen through said nozzle.

5. The system according to claim 1 wherein said collection sponge comprises a swab and a stem interconnecting the piston and said swab.

6. The system according to claim 1 wherein said elongate enclosure includes vents.

7. The system according to claim 1 wherein said specimen capsule further comprises an active agent for reacting with said specimen.

8. The system according to claim 1 wherein the capsule cap includes a nozzle and a nozzle cap.

9. The system according to claim 8 wherein said specimen capsule is squeezable for enabling dispensing of specimen through said nozzle.

10. The system according to claim 1 wherein said collection sponge comprises a swab and a stem interconnecting the piston and said swab.

11. The system according to claim 1 wherein said specimen capsule further comprises an active agent for reacting with said specimen.

12. A bio-molecular sampling and transportation system utilizing a docking mechanism, the system comprising:
    an elongate enclosure having open ends;
    a collection sponge, including a swab and a stem, slideably disposed within said elongate enclosure;
    a sponge moving piston, disposed within said elongate enclosure, and attached to said stem, having an engagable end disposed proximate one end of said elongate enclosure;
    a tubular plunger handle storable within said elongate enclosure between said collection sponge and an inside of said enclosure and engagable with the piston for enabling manual sliding of said collection sponge between a position inside of said elongate enclosure and a position exterior another end of said elongate enclosure;

a specimen capsule, removably dockable to the another end of said elongate enclosure, for receiving specimen from said collection sponge, said specimen capsule including a perforated baffle, the baffle perforation enabling passage of specimen therepast into said specimen capsule upon compressing of said collection sponge thereagainst by the piston via said plunger handle;

removable enclosure caps for sealing said elongate enclosure; and a removable specimen capsule cap for sealing said specimen capsule.

13. The system according to claim 12 further comprising a connector for removably docking said specimen capsule to said elongate enclosure.

14. The system according to claim 12 wherein the capsule cap includes a nozzle and a nozzle cap.

15. The system according to claim 14 wherein said specimen capsule is squeezable for enabling dispensing of specimen through said nozzle.

16. The system according to claim 12 wherein said specimen capsule further comprises an active agent for reacting with said specimen.

17. A method for bio-molecular sampling and transporting comprising:

providing an elongate enclosure with a collection sponge slideably disposed within said elongate enclosure and a tubular plunger handle storable within said elongate enclosure between said collection sponge and an inside of said elongate enclosure;

removing the handle from said elongate enclosure;

attaching the handle to a plunger fixed to said collection sponge;

manually sliding of said collection sponge with the plunger and handle to an extended position exterior another end of said elongate enclosure;

absorbing specimen with the extended sponge;

retracting the sponge into the enclosure with the plunger and handle;

docking a specimen capsule, to the enclosure, for receiving specimen from said collection sponge;

compressing said collection sponge to force specimen into the capsule; and sealing said specimen capsule.

18. The method according to claim 17 further comprising attaching a nozzle to the capsule and squeezing the capsule to dispose specimen through the nozzle.

* * * * *